(12) United States Patent
Chen et al.

(10) Patent No.: US 11,357,852 B2
(45) Date of Patent: Jun. 14, 2022

(54) DIGLYCOSYLATED BENZOPHENOXAZINE PHOTOSENSITIZER AND PREPARATION METHOD AND USE THEREOF

(71) Applicant: The Third Xiangya Hospital of Central South University, Changsha (CN)

(72) Inventors: Jing Chen, Changsha (CN); Jinhua Huang, Changsha (CN); Jian Kang, Changsha (CN); Zhen Wang, Changsha (CN); An Liu, Changsha (CN); Xiangzhi Song, Changsha (CN); Kehua Guo, Changsha (CN); Siqi Ma, Changsha (CN); Jian Huang, Changsha (CN); Liyang Kang, Changsha (CN); Chengxin Zuo, Changsha (CN); Shengbo Yang, Changsha (CN); Yihao Li, Changsha (CN); Jiahao Li, Changsha (CN); Jiayao Pan, Changsha (CN); Guishao Tang, Changsha (CN)

(73) Assignee: The Third Xiangva Hospital of Central South University, Changsha (CN)

( * ) Notice: Subject to any disclaimer, the term of this patent is extended or adjusted under 35 U.S.C. 154(b) by 164 days.

(21) Appl. No.: 16/763,489

(22) PCT Filed: Nov. 16, 2017

(86) PCT No.: PCT/CN2017/111282
§ 371 (c)(1),
(2) Date: May 12, 2020

(87) PCT Pub. No.: WO2019/090802
PCT Pub. Date: May 16, 2019

(65) Prior Publication Data
US 2020/0297846 A1    Sep. 24, 2020

(30) Foreign Application Priority Data

Nov. 13, 2017 (CN) .......................... 201711118656.3

(51) Int. Cl.
*A61K 41/00* (2020.01)
*A61P 35/00* (2006.01)

(52) U.S. Cl.
CPC .......... *A61K 41/0057* (2013.01); *A61P 35/00* (2018.01)

(58) Field of Classification Search
CPC ....... A61K 41/0057; A61P 35/00; A61P 35/04
See application file for complete search history.

(56) References Cited

U.S. PATENT DOCUMENTS

| 2004/0116508 A1* | 6/2004 | Walker ................. C07D 335/16 514/434 |
| 2008/0015189 A1 | 1/2008 | Hamblin et al. |

FOREIGN PATENT DOCUMENTS

| CN | 103755753 A | 4/2014 |
| CN | 107759642 A | 3/2018 |
| WO | 0183621 A2 | 11/2001 |

OTHER PUBLICATIONS

Fang et al., "The Synthesis and Properties of the Water-soluble Benzo[a]phenoxazinium Chalcogen with Heteroatom (O, S, Se) as Photosensitizers", Engineering Science & Technology I, Chinese Master's Theses Full-text Database (2013).
Soares et al., "Synthesis of water-soluble phthalocyanines bearing four or eight d-galactose units", Carbohydrate Research, vol. 344, pp. 507-510 (2009).
Sun, "Abnormal glycometabolism in tumor cells", Journal of International Oncology, vol. 40, No. 12, pp. 883-885 (2013).
English-language abstract of CN103755753 (2014).
English-language abstract of CN107759642 (2018).
International Search Report for PCT/CN2017/111282 dated Jul. 20, 2018.

* cited by examiner

*Primary Examiner* — Pancham Bakshi
(74) *Attorney, Agent, or Firm* — Caesar Rivise, PC

(57) ABSTRACT

Disclosed are a diglycosylated benzophenoxazine photosensitizer, and a preparation method and use thereof. The present invention greatly improves the enriched concentration of the photosensitizer in tumor cells by taking full advantage of the enhanced uptake and enhanced glycolysis of carbohydrates by tumor cells and the glycosylation of a selenium-containing benzophenoxazine compound, thereby improving the targeting of a diglycosylated benzophenoxazine photosensitizer involved in the present invention in the treatment of cutaneous tumors and also significantly decreasing the toxic and side effects of the photodynamic therapy. The present invention can efficiently and rapidly inhibit the proliferation of cells of cutaneous squamous cell carcinoma and essentially cause no damage to normal cells.

8 Claims, 3 Drawing Sheets

DIGLYCOSYLATED BENZOPHENOXAZINE PHOTOSENSITIZER AND PREPARATION METHOD AND USE THEREOF

CROSS-REFERENCE TO RELATED APPLICATIONS

This application is the U.S. National Phase Application of PCT/CN2017/111282, filed Nov. 16, 2017, which claims priority from CN 201711118656.3, filed Nov. 13, 2017, the contents of which applications are incorporated herein by reference in their entireties for all purposes.

FIELD OF THE INVENTION

The present invention relates to a diglycosylated benzophenoxazine photosensitizer, and a preparation method and use thereof.

BACKGROUND OF THE INVENTION

Photodynamic Therapy (PDT) is a new method for treating malignant tumors developed in the last 20 years. It has a relatively selective specificity for tumors, can directionally eliminate primary and recurrent tumors, and has many advantages such as small toxic and side effects, no scar formation, easy operation and control, etc. At the same time, it also protects a patient from the danger of general anesthesia, and it is simple and easy to operate under simple local anesthesia. The photosensitizer is the core component of the PDT. The performance and characteristics of the photosensitizer determine the size of the therapeutic effect of the PDT. The ideal photosensitizer for the PDT should have the following characteristics: 1) strong absorption in a phototherapy window of 600-800 nm; 2) a high singlet oxygen yield; 3) strong phototoxicity and low darkness; 4) a certain tumor-targeting ability; and 5) determined components. The benzophenoxazine photosensitizer studied at present is developed from phenoxazine dyes containing selenium atoms, and has the advantages of an absorption wavelength above 650 nm and a high absorption intensity. However, as a molecule with photosensitization developed directly from an industrial dye, it also has certain problems during the process of the PDT for humans. For example, the photosensitizer containing selenium atoms as studied in the paper (Fang Qian, "The Synthesis and Properties of the Water-soluble Benzo[a]Phenoxazinium Chalcogen Analogues with Heteroatom (O, S, Se) as Photosensitizers" [D]. Central South University, 2012) has an efficient photodynamic effect, but it has not been further designed and optimized in combination with metabolism and uptake characteristics of organisms or tumors. Otto Warburg, a German biochemist, proposed that the biochemical characteristic of tumor cells is the transformation of glycometabolism from oxidative phosphorylation to aerobic glycolysis, i.e., the Warburg effect. The metabolic pathway of glycolysis is conducive to the rapid proliferation of the tumor cells. The tumor cells can obtain intermediate metabolites through glycolysis to meet their own active synthesis needs. A paper (Jie SUN; Xiangjun MENG, "Abnormal glycometabolism in tumor cells" [J]. Journal of International Oncology, 2013, (12): 883-885) also elaborated: the tumor cells have a special tendency of uptaking carbohydrates, i.e., the viewpoint that during the metabolic process of tumor tissues, the intake of monosaccharides such as glucose and galactose increases, and the aerobic glycolysis is enhanced. The tendency of uptaking carbohydrates and metabolic characteristics of the tumor cells provide an entirely new idea for the treatment of tumors and the development of anti-tumor drugs. Meanwhile, the Wnt signaling pathway can cause the accumulation of intracellular β-catenin. β-catenin (referred to as an Armadillo protein in drosophila) is a multifunctional protein. It interacts with cadherin at cell junctions to participate in the formation of an adhesive strip, while free β-catenin can enter the nucleus to regulate gene expression. The β-catenin protein cannot be degraded by phosphorylation and ubiquitination, such that it is accumulated in large amounts in cytoplasm, and thus enters the nucleus and activates genes related to cell division and growth regulation (such as c-myc, Cyclin D1, and the like genes), leading to carcinogenesis due to uncontrolled cell proliferation. Therefore, people begin to try to use key proteins in the Wnt/β-Catenin signaling pathway as drug targets to screen molecular drugs for cancer treatment. The research on the synergetic mechanism of intracellular signaling pathways can provide a more theoretical basis for us to design a more effective anti-cancer drug.

SUMMARY OF THE INVENTION

Aiming at the above technical problems and based on the special metabolic characteristics of tumor cells, in the present invention a high-efficiency selenium-containing benzophenoxazine photosensitizer is subjected to double saccharification modification, so that the modified selenium-containing benzophenoxazine photosensitizer conforms to the uptake and metabolic characteristics of the tumor cells in chemical structure, thereby being better concentrated in the tumor cells to increase the photodynamic therapy effect and targeting property. An objective of the present invention is to provide a diglycosylated benzophenoxazine photosensitizer which is more suitable for cutaneous tumor treatment and has a stronger targeting property, and a preparation method thereof. The technical solution of the present invention is to provide a diglycosylated benzophenoxazine photosensitizer having a structural formula below:

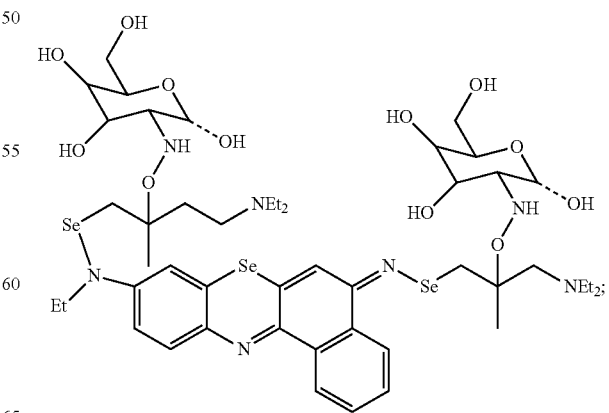

wherein, Et represents ethyl.

The present also provides a method for preparing the aforementioned diglycosylated benzophenoxazine photosensitizer, including the following steps:

(1) reacting galactose with a selenium-containing compound

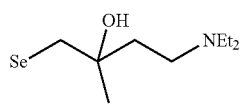

in a solvent of ethanol at 65° C.-68° C. to obtain a selenium-containing glycosylated compound, wherein the reaction process is as follows:

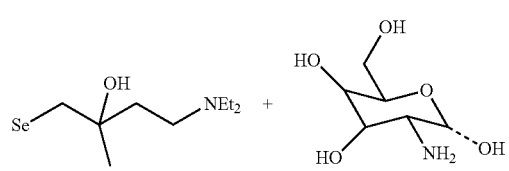

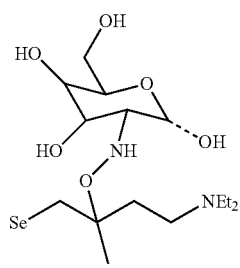

(2) reacting

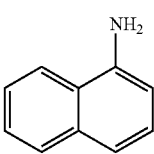

with the selenium-containing glycosylated compound obtained in the step (1) in a solvent of acetone under the conditions of 160° C.-165° C. to obtain an intermediate product A, wherein the reaction formula is:

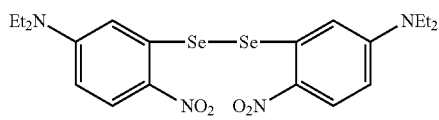
+

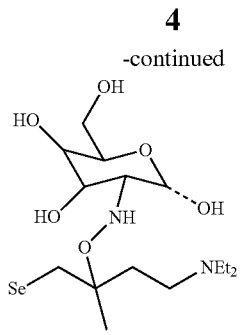

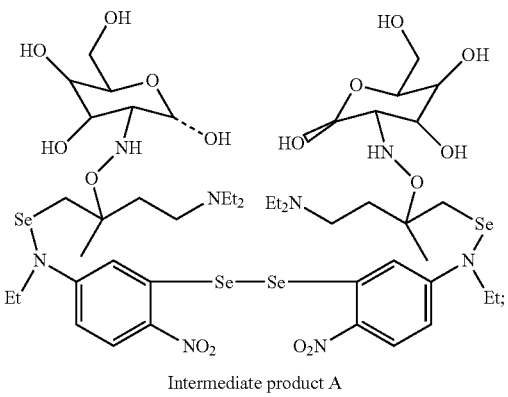

Intermediate product A reacting 1-naphthylamine with the selenium-containing glycosylated compound obtained in the step (1) in a solvent of ethanol by heating to reflux, so as to obtain an intermediate product B, wherein the reaction process is:

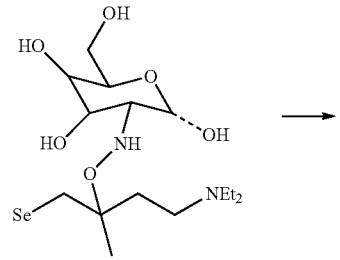

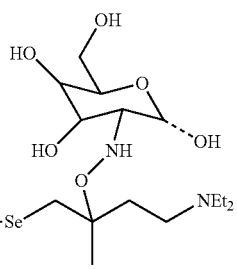

Intermediate product B (3) reacting the intermediate product A and the intermediate product B obtained in the step (2) under a condition of 85° C.-90° C. in a solvent of toluene, wherein the reaction process is as follows:

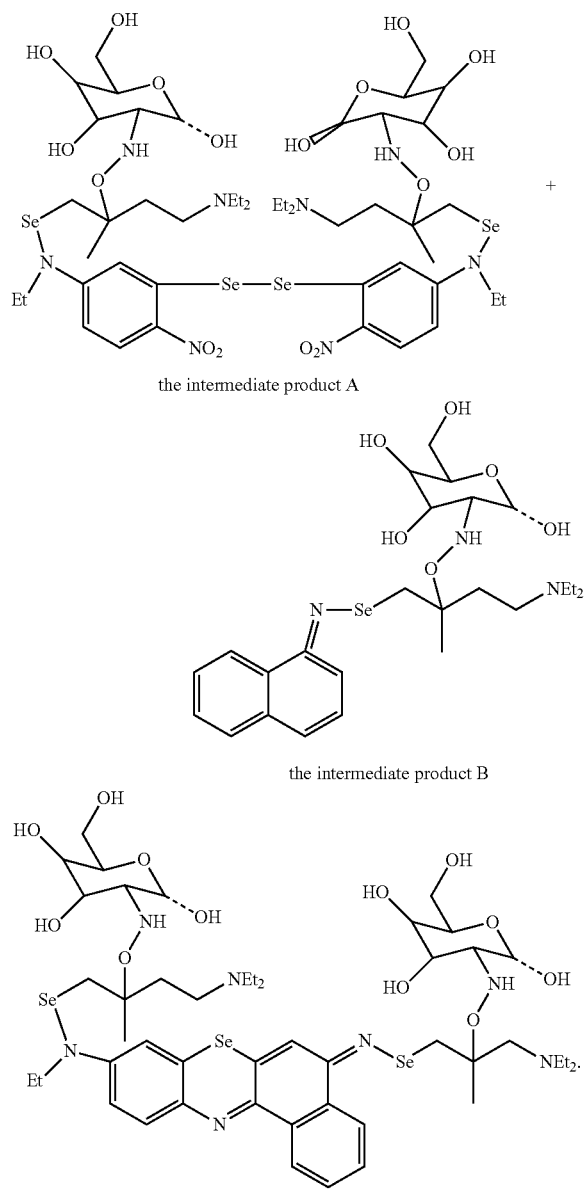

the intermediate product A the intermediate product B

Preferably, in the step (1), the molar ratio of galactose to the selenium-containing compound is 1-1.5:3-34; and the reaction time is 5-8 minutes.

Preferably, in the reaction of preparing the intermediate product A in the step (2), the reaction time is 25-35 minutes; and the molar ratio of

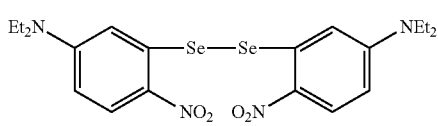

to the selenium-containing compound is 1:2.5-36.

Preferably, in the reaction for preparing the intermediate product B in the step (2), the temperature of the solvent of ethanol is 65° C.-70° C.

Preferably, in the reaction of preparing the intermediate product B in the step (2), the molar ratio of the 1-naphthylamine to the selenium-containing glycosylated compound is 2-2.5:1-1.5.

Preferably, in the step (3), the reaction time is 5-6 minutes; and the molar ratio of the intermediate product A to the intermediate product B is 1:1.

The present invention also provides use of the diglycosylated benzophenoxazine photosensitizer in the preparation of an anti-tumor drug.

The photosensitizer of the present invention can inhibit the proliferation of cells of cutaneous squamous cell carcinoma through a Wnt/β-catenin signaling pathway, thereby effectively killing and inhibiting the cells of cutaneous squamous cell carcinoma. In the process of human cutaneous tumors, the dosage of a diglycosylated benzophenoxazine photosensitizer involved in the present invention is 5-35 mg/kg; the wavelength range of the exciton light source used for exciting the photosensitizer is 550-780 nm, and preferably 625 nm; and the light intensity of the excitation light source used for exciting the photosensitizer is 5-25 $J/cm^2$, and preferably 8.5 $J/cm^2$. The utilized light source is: one or more of an ultrasonic irradiation generator, a light emitting tube, a laser tube, a fuel laser, a halogen metal lamp, a flash lamp, a mechanically-filtered fluorescent light source, daylight or mechanically-filtered daylight, or an incandescent line light source, and preferably the laser tube is used. The beneficial effect of the present invention is that the present invention greatly improves the enriched concentration of the photosensitizer in tumor cells by taking full advantage of the metabolic characteristics of tumor cells, i.e., the enhanced uptake and enhanced glycolysis of carbohydrates by tumor cells, and the glycosylation of a selenium-containing benzophenoxazine compound, thereby improving the targeting of a diglycosylated benzophenoxazine photosensitizer involved in the present invention in the treatment of cutaneous tumors and also significantly decreasing the toxic and side effects of the photodynamic therapy. The present invention can efficiently and rapidly inhibit the proliferation of cells of cutaneous squamous cell carcinoma and essentially cause no damage to normal cells.

DETAILED DESCRIPTION OF EMBODIMENTS

The present invention will be further described below with reference to examples.

Example 1: Synthesis of the Diglycosylated Benzophenoxazine Photosensitizer (1) galactose was reacted with a selenium-containing compound

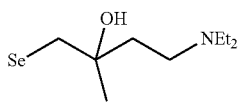

in a solvent of ethanol at 65° C.-68° C. for 5-8 minutes at a dosage ratio of galactose to the selenium-containing compounds of 1-1.5:3-34, wherein the reaction process was as follows:

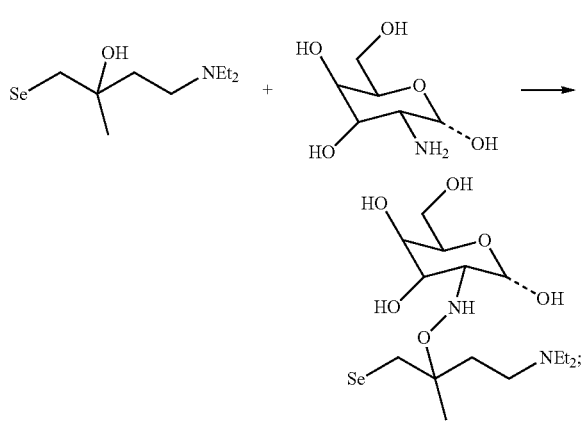

(2) The selenium-containing glycosylated compound obtained in the step (1) was reacted with

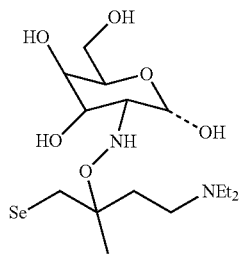

in a solvent of acetone under the conditions of 160° C.-165° C. for 30 minutes, wherein the reaction process was:

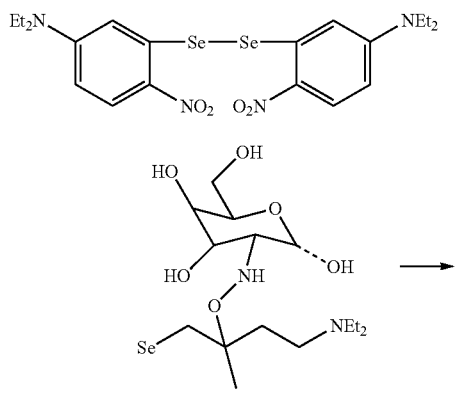

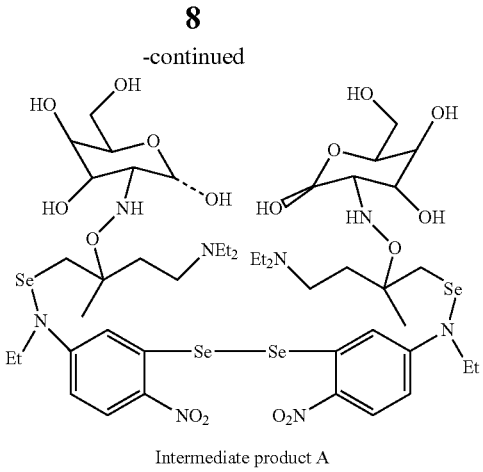

Intermediate product A (3) 1-naphthylamine was reacted with the glycosylated selenium-containing compound

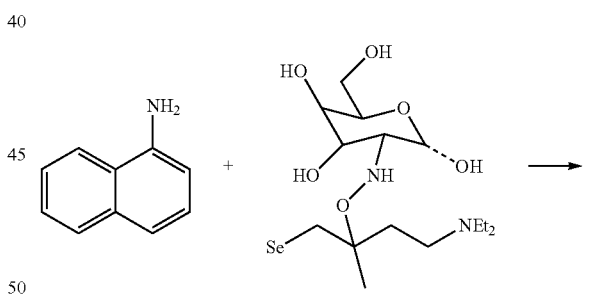

obtained in the step (1) at a dosage ratio of the 1-naphthylamine to the glycosylated selenium-containing compound of 2-2.5:1-1.5 in a solvent of ethanol at 85° C.-87° C. for 15-20 minutes, wherein the reaction process was:

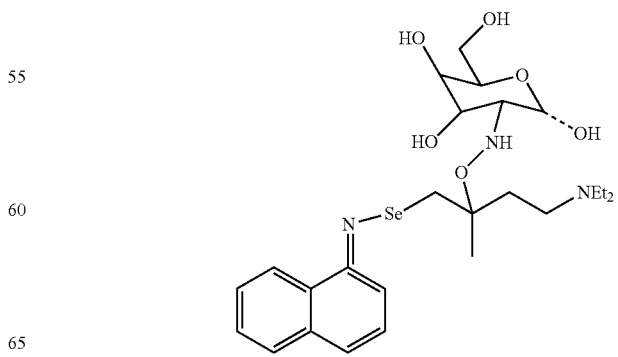

(4) The product obtained in the step (3) was reacted with the product obtained in the step (2) under the conditions of 160° C.-170° C. in acetone or toluene as the solvent for 5-6 minutes, wherein the ratio of the two reactants was 1:1, and the reaction process was:

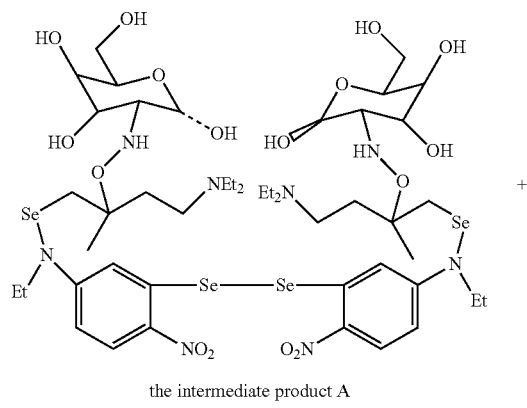

the intermediate product A

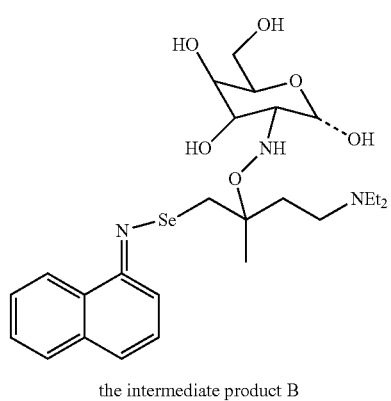

the intermediate product B

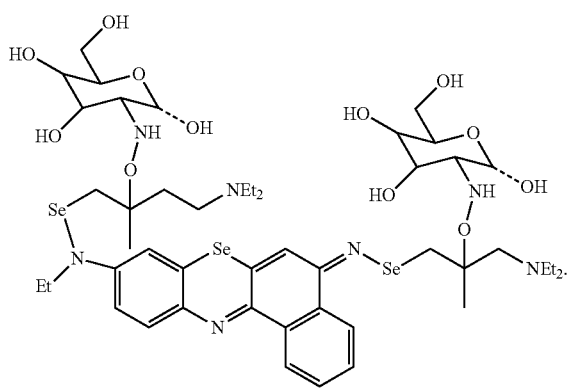

Figure 1:
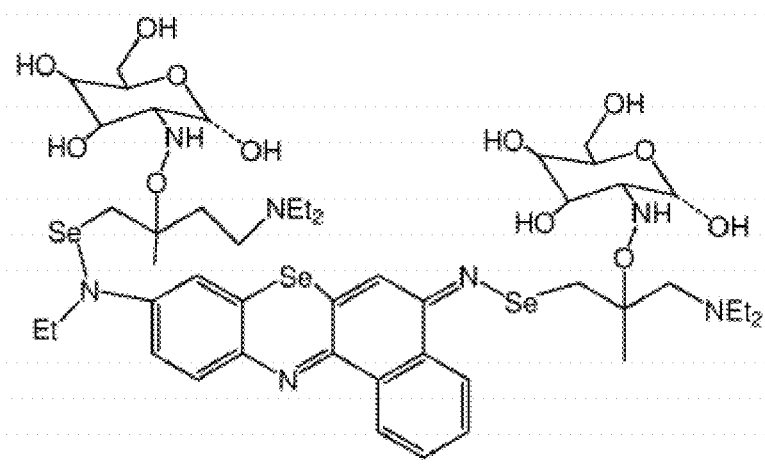
FIG. 1 shows the structural formula of a diglycosylated benzophenoxazine photosensitizer.
Figure 2:
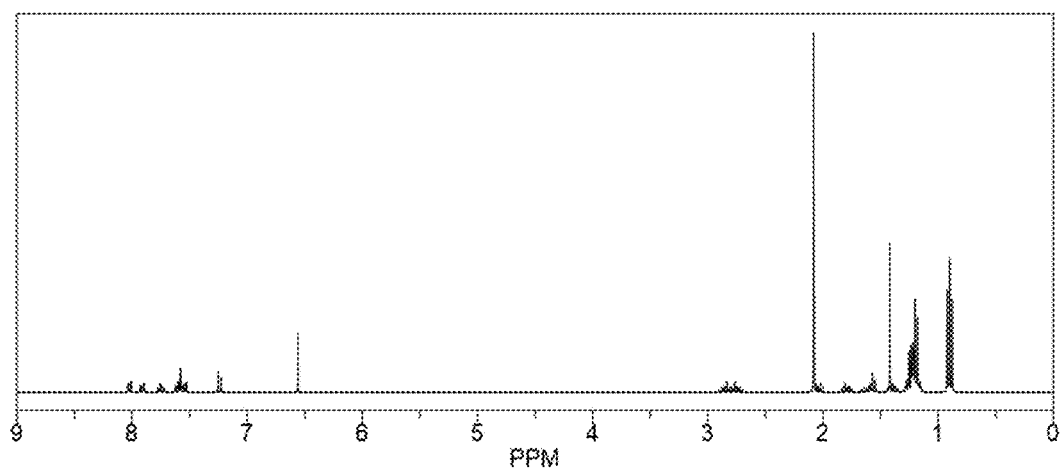
FIG. 2 shows the hydrogen spectrogram of the diglycosylated benzophenoxazine photosensitizer.
Figure 3:
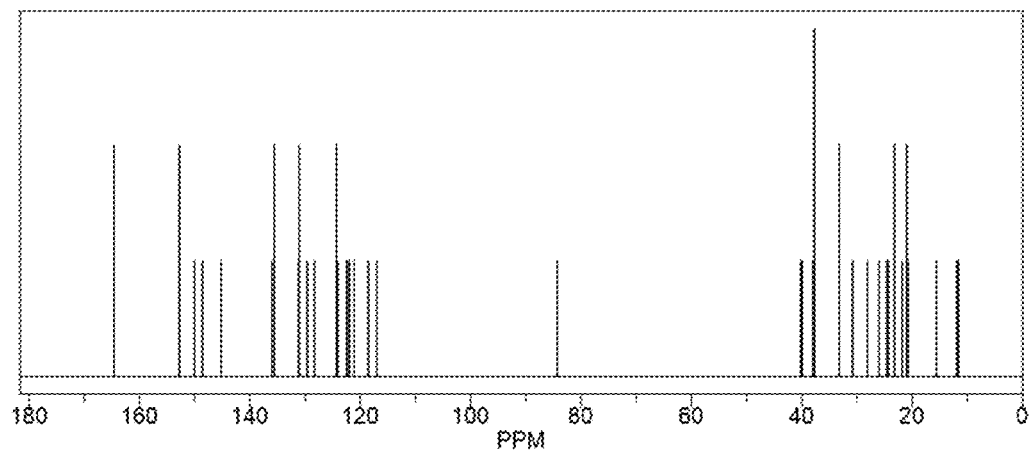
FIG. 3 shows the carbon spectrogram of the diglycosylated benzophenoxazine photosensitizer.

The hydrogen spectrogram and carbon spectrogram of the aforementioned diglycosylated benzophenoxazine photosensitizer were shown in FIGS. 2 and 3, respectively. It could be confirmed that the present invention successfully synthesized the aforementioned target product.

Example 2 Inhibition of Proliferation of Cells of Cutaneous Squamous Cell Carcinoma by a Diglycosylated Benzophenoxazine Photosensitizer The MTT method is a method for detecting cell survival and growth. The detection principle of it is that a succinate dehydrogenase in mitochondria of living cells can reduce exogenous MTTs to water-insoluble blue-violet crystalline formazan and deposit the formazan in the cells, while dead cells have no such function. Dimethyl sulfoxide (DMSO) can dissolve the formazan in the cells, and the light absorbance value of it is measured at 490 nm wavelength with an enzyme-linked immunometric meter, which can indirectly reflect the number of living cells.

(1) Experimental Method

The cell line A-431 of cutaneous squamous cell carcinoma was cultured in a DMEM medium that contained 10% calf serum, added with 100 IU/L of penicillin and 100 mg/L of streptomycin, and placed in a constant-temperature incubator at 37° C. and containing 5% $CO_2$ for conventional culture. After the cells grew to confluence on the bottom of the flask, the medium was discarded, the cells were rinsed twice with a PBS solution, and then digested with 0.25% trypsin and 0.02% EDTA for 5 minutes, and then subcultured into flasks once every 2 to 3 days. The cells at the logarithmic growth phase were taken for experiment.

A-431 cells at the logarithmic growth phase were digested with trypsin, and inoculated into a six-well culture plate, and cultured in a 5% $CO_2$ incubator at 37° C. When grew to the confluence of 80%-90%, the cells were respectively added with distilled water and 100 nM, 200 nM, 400 nM, 600 nM and 800 nM of the diglycosylated benzophenoxazine photosensitizer referred in the present invention. After incubation for 1 h, the cells were irradiated with 20 $J/cm^2$ of red light for 15 min. 16 h later, the survival and growth status of the cells were detected by the MTT method.

(2) Experimental Result

Figure 4:
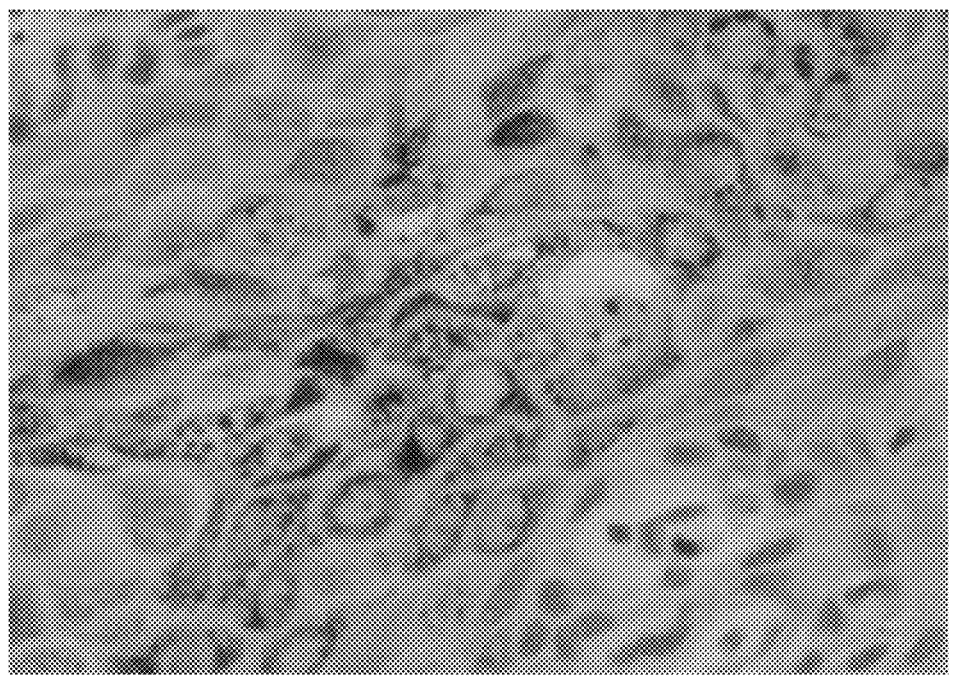
FIG. 4 is a diagram showing the pathological sections of a tumor tissue after the external treatment with the photosensitizer.

The MTT experimental results show that, the diglycosylated benzophenoxazine photosensitizer referred in the present invention can significantly inhibit the proliferation of the A-431 cells, and as the dose of the photosensitizer increases, the inhibition effect on cell proliferation increases. The diglycosylated benzophenoxazine photosensitizer referred in the present invention can achieve a proliferation inhibition effect of 80% at 800 nM. At the same time, the pathological detection results show that the diglycosylated benzophenoxazine photosensitizer referred in the present invention can be specifically enriched in the cells of cutaneous squamous cell carcinoma, and is more concentrated on the membrane structures of important organelles such as the nuclear envelope and endoplasmic reticulum membrane (FIG. 4).

Example 3: Inhibition of Proliferation of A-431 Cells by the Diglycosylated Benzophenoxazine Photosensitizer by Inhibiting Wnt Signaling The Wnt signaling pathway mainly refers to a classic Wnt signaling pathway mediated by β-Catenin. In the absence of the Wnt signaling, GSK3β can add a phosphate group to the serine/threonine residue at the N-terminus of β-Catenin. The phosphorylated β-Catenin is covalently modified by β-TRCP ubiquitination and then degraded by a proteasome. PP2A dephosphorylation of GSK3β in the Wnt pathway can significantly promote the Wnt signaling. Therefore, by measuring the phosphorylation statuses of GSK3β, β-Catenin and PP2A, we can directly understand whether the Wnt signaling is activated. C-myc and Cyclin D1 as protooncogenes can promote division and translation of the cells of cutaneous squamous cell carcinoma, and ultimately promote cell proliferation. By observing C-myc and Cyclin D1, we can clearly understand the inhibition effect of the photosensitizer of the present invention on proliferation of the A-431 cells.

(1) Experimental Method

The cell line A-431 of cutaneous squamous cell carcinoma was cultured in a DMEM medium that contained 10% calf serum, added with 100 IU/L of penicillin and 100 mg/L of streptomycin, and placed in a constant-temperature incubator at 37° C. and containing 5% $CO_2$ for conventional culture. After the cells grew to confluence on the bottom of the flask, the medium was discarded, the cells were rinsed twice with a PBS solution, and then digested with 0.25% trypsin and 0.02% EDTA for 5 minutes, and then subcultured into flasks once every 2 to 3 days. The cells at the logarithmic growth phase were taken for experiment.

A-431 cells at the logarithmic growth phase were digested with trypsin, and inoculated into a six-well culture plate, and cultured in a 5% $CO_2$ incubator at 37° C. When grew to the confluence of 80%-90%, the cells in each well were added with the diglycosylated benzophenoxazine photosensitizer referred in the present invention until the final concentrations were respectively 0 nM, 100 nM, 200 nM, 400 nM, and 800 nM. After incubation for 1 h, the cells were irradiated with 20 $J/cm^2$ of red light for 15 min. Respectively after 0.5 h and 16 h, the cells were collected to extract total protein, and the p-GSK3β, p-PP2A, p-β-catenin, C-myc, Cyclin D1 and β-Catenin in the cells were detected by the Western Blot method.

(2) Experimental Result

Figure 5:
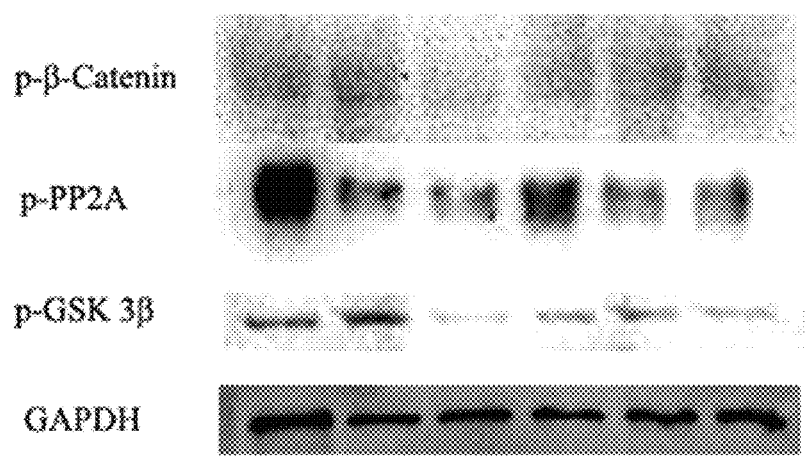
FIG. 5 is a graph showing Western Blot results of cell proliferation signaling proteins after the treatment with the photosensitizer.
Figure 6:
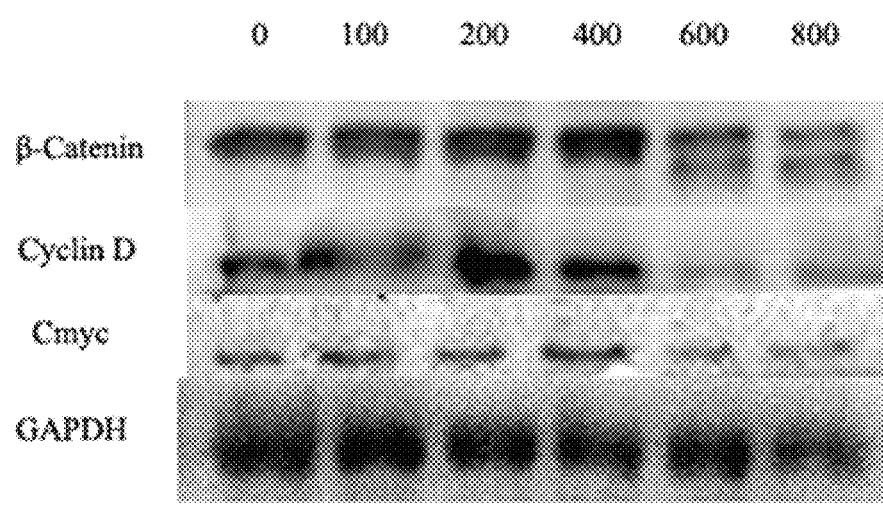
FIG. 6 is a graph showing Western Blot results of cell proliferation-related proteins after the treatment with the photosensitizer.

By analysis of Western Blot results of GSK3β, PP2A, β-catenin phosphorylation of the A-431 cells treated with gradient doses of the diglycosylated benzophenoxazine photosensitizer, it is found that the photosensitizer doses of 200 to 800 nM can significantly inhibit the phosphorylation of PP2A and GSK3β. The 100 nM and 400 to 800 nM of the diglycosylated benzophenoxazine photosensitizer referred in the present invention can significantly promote the phosphorylation of β-catenin (FIG. 5). By analysis of the Western Blot results of the expression quantities of β-catenin, Cyclin D1 and C-myc in A-431 cells treated with the gradient doses of the diglycosylated benzophenoxazine photosensitizer, it is found that the expression quantities of β-Catenin, Cyclin D1 and C-myc are increased slightly after treatment with the diglycosylated benzophenoxazine photosensitizer at doses of 100 to 400 nM, but significantly decreased after treatment with the diglycosylated benzophenoxazine photosensitizer at doses of 600 and 800 nM. The results indicate that 600 nM and 800 nM of the diglycosylated benzophenoxazine photosensitizer can significantly inhibit the proliferation of A-431 cells (FIG. 6).

The invention claimed is:

1. A diglycosylated benzophenoxazine photosensitizer having a structural formula as follows:

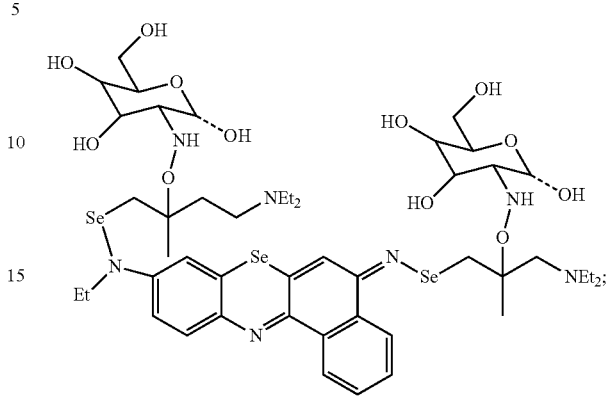

wherein, Et represents ethyl.

2. A method for preparing the diglycosylated benzophenoxazine photosensitizer according to claim 1, comprising the following steps:
   (1) reacting galactose with a selenium-containing compound (compound 1) in a solvent of ethanol at 65° C.-68° C. to obtain a glycosylated selenium-containing compound (compound 2);
   (2) reacting with the glycosylated selenium-containing compound obtained in step (1) in a solvent of acetone at a temperature of 160° C.-165° C. to obtain an intermediate product A;
   reacting 1-naphthylamine with the glycosylated selenium-containing compound obtained in step (1) in a solvent of ethanol by heating to reflux, so as to obtain an intermediate product B;
   (3) reacting the intermediate product A and the intermediate product B obtained in step (2) at a temperature of 85° C.-90° C. in a solvent of toluene, so as to obtain the diglycosylated benzophenoxazine photosensitizer;
   wherein the structural formulas of Compound 1, Compound 2, Compound 3, Intermediate Product A, and Intermediate Product B are:
   Intermediate Product B.

3. The method according to claim 2, wherein in step (1), a molar ratio of galactose to the glycosylated selenium-containing compound is 1-1.5:3-34; and a reaction time is 5-8 minutes.

4. The method according to claim 2, wherein in the reaction of preparing the intermediate product A step (2), a reaction time is 25-35 minutes; and a molar ratio of

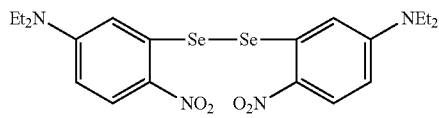

to the glycosylated selenium-containing compound is 1:2.5-3.6.

5. The method according to claim 2, wherein in the reaction of preparing the intermediate product B in step (2), a temperature of the solvent of ethanol is 65° C.-70° C.

6. The method according to claim 2, wherein in the reaction of preparing the intermediate product B in step (2), a molar ratio of the 1-naphthylamine to the glycosylated selenium-containing compound is 2-2.5:1-1.5.

7. The method according to claim 2, wherein in step (3), a reaction time is 5-6 minutes; and a molar ratio of the intermediate product A to the intermediate product B is 1:1.

8. An anti-tumor drug comprising the diglycosylated benzophenoxazine photosensitizer according to claim 1.

\* \* \* \* \*